(12) United States Patent
Kley

(10) Patent No.: US 7,776,893 B2
(45) Date of Patent: Aug. 17, 2010

(54) USE OF PDE4 INHIBITORS FOR THE TREATMENT OF DIABETES MELLITUS

(75) Inventor: Hans-Peter Kley, Allensbach (DE)

(73) Assignee: NYCOMED GmbH, Constance (DE)

( * ) Notice: Subject to any disclaimer, the term of this patent is extended or adjusted under 35 U.S.C. 154(b) by 311 days.

(21) Appl. No.: 10/570,622

(22) PCT Filed: Sep. 2, 2004

(86) PCT No.: PCT/EP2004/052005

§ 371 (c)(1),
(2), (4) Date: Mar. 3, 2006

(87) PCT Pub. No.: WO2005/023253

PCT Pub. Date: Mar. 17, 2005

(65) Prior Publication Data

US 2006/0281745 A1    Dec. 14, 2006

(30) Foreign Application Priority Data

Sep. 5, 2003    (EP) .................... 03020126

(51) Int. Cl.
*A61K 31/44* (2006.01)
*A61K 31/165* (2006.01)

(52) U.S. Cl. .............. 514/352; 514/617; 514/866
(58) Field of Classification Search ......... 514/352, 514/617, 866
See application file for complete search history.

(56) References Cited

U.S. PATENT DOCUMENTS

| 5,712,298 | A * | 1/1998 | Amschler ............ 514/352 |
|---|---|---|---|
| 5,730,975 | A | 3/1998 | Hotamisligil et al. |
| 5,817,670 | A | 10/1998 | Takayama et al. |
| 6,011,060 | A | 1/2000 | Laurent et al. |
| 6,191,138 | B1 | 2/2001 | Gutterer |
| 6,255,326 | B1 | 7/2001 | Ashton et al. |
| 6,331,543 | B1 | 12/2001 | Garvey et al. |
| 6,924,292 | B2 | 8/2005 | Kawano et al. |
| 7,109,342 | B2 | 9/2006 | Nakai et al. |
| 2002/0002191 | A1 | 1/2002 | Friesen et al. |
| 2003/0023087 | A1 | 1/2003 | Garvey et al. |
| 2003/0069169 | A1 | 4/2003 | Macor et al. |
| 2003/0186974 | A1 | 10/2003 | Marfat et al. |
| 2004/0087591 | A1 | 5/2004 | Garvey et al. |
| 2004/0235845 | A1 | 11/2004 | Eggenweiler et al. |
| 2005/0049258 | A1 | 3/2005 | Marfat et al. |

| 2005/0130891 | A1 | 6/2005 | Forssmann et al. |

FOREIGN PATENT DOCUMENTS

| DE | 101 50 517 A1 | 4/2003 |
|---|---|---|
| EP | 0300726 B1 | 9/1993 |
| JP | 58-69812 | 4/1983 |
| WO | 94/02150 A1 | 2/1994 |
| WO | 94/02465 A1 | 2/1994 |
| WO | 95/01338 A1 | 1/1995 |
| WO | 97/28131 A1 | 8/1997 |
| WO | 99/14239 A1 | 3/1999 |
| WO | 00/42020 A1 | 7/2000 |
| WO | 00/42034 A1 | 7/2000 |
| WO | 01/35979 A2 | 5/2001 |
| WO | 0142244 A1 | 6/2001 |
| WO | 0170746 A1 | 9/2001 |
| WO | 0190076 A1 | 11/2001 |
| WO | 02/13798 A2 | 2/2002 |
| WO | 0214280 A1 | 2/2002 |
| WO | 02/064584 A1 | 8/2002 |
| WO | 02074726 A2 | 9/2002 |
| WO | 03/032993 A1 | 4/2003 |
| WO | 03061638 A2 | 7/2003 |
| WO | WO 2004/016596 | 2/2004 |
| WO | 2004067006 A1 | 8/2004 |
| WO | 2004/098595 A1 | 11/2004 |
| WO | 2004/098596 A1 | 11/2004 |
| WO | 2004/098597 A1 | 11/2004 |
| WO | 2004/098598 A1 | 11/2004 |
| WO | 2004103407 A2 | 12/2004 |
| WO | 2005020926 A2 | 3/2005 |
| WO | 2005116653 A2 | 12/2005 |

OTHER PUBLICATIONS

Liang, L, et al., "The Phosphodiesterase Inhibitors Pentoxifylline and Rolipram Prevent Diabetes in NOD Mice", *Diabetes*, vol. 47, pp. 570-575, (1998).
U.S. Appl. No. 11/885,450, Kley et al., filed Aug. 31, 2007.
Leibowitz et al, A Novel Insulin Secretagogue Is a Phosphodiesterase Inhibitor, Diabetes, 44:67-74, 1995.
Ceriello et al., Postprandial Glucose Regulation and Diabetic Complications, Arch. Intern. Med., 164:2090-2095, 2004.
"Postprandial Hyperglycemia and Cardiovascular Disease", Gerich, John, Endocrine Practice, vol. 12, Supplement 1, Jan./Feb. 2006, pp. 47-51.

* cited by examiner

*Primary Examiner*—Kevin Weddington
(74) *Attorney, Agent, or Firm*—The Nath Law Group; Joshua B. Goldberg; Sheldon M. McGee

(57) ABSTRACT

The invention relates to the use of certain known PIDE4 inhibitors for the treatment of diabetes mellitus and accompanying disorders thereof.

8 Claims, No Drawings

USE OF PDE4 INHIBITORS FOR THE TREATMENT OF DIABETES MELLITUS

TECHNICAL FIELD

The invention relates to the use of certain known PDE4 inhibitors for the treatment of diabetes mellitus and accompanying disorders thereof.

PRIOR ART

In the International Patent Application WO99/14239 compositions for treating diabetes mellitus and obesity are disclosed. The compositions contain at least two of the active agents A, B and C, wherein A is at least one hormon which stimulates the production of cAMP, B is at least one substance which inhibits the breakdown of a cyclic nucleotide, and C is at least one hormon which stimulates the production of cGMP. In the International Patent Application WO01135979 the combined use of a PDE3 and a PDE4 inhibitor for the treatment of obesity is disclosed. In the International Patent Application WO02/13798 the use of a selective cGMP PDE5 inhibitor for the treatment of Insulin Resistance Syndrome is disclosed, wherein the Insulin Resistance Syndrome is defined as the cocomitant existence of two or more disease states selected from dyslipidemia, hypertension, type 2 diabetes mellitus, impaired glucose tolerance, a family history of diabetes, hyperuricaemia and/or gout, a pro-coalgulant state, atherosclerosis and truncal obesity. In the unexamined german application DE 10150517 tetrahydropyridazin-3-one derivatives are described which may be useful inter alia for the treatment of diabetes mellitus. In Diabetes 47, pp. 570-575, 1998 is disclosed that pentoxyfylline and rolipram may be effective in the treatment of autoimmune diabetes or other conditions characterized by excessive production of inflammatory cytokines.

BACKGROUND OF THE INVENTION

Diabetes mellitus is on the rise worldwide and is considered to be at an epidemic level by the World Health Organization. The clinical manifestation and progression of diabetes often vary considerably between countries and commonly between ethnic groups in the same country. Currently diabetes affects 151 million people worldwide and an estimate 300 million people in 2025. There are two main forms of diabetes. Type 1 (insulin-dependent diabetes mellitus, IDDM) is due primarily to autoimmune-mediated destruction of pancreatic β-cells, resulting in absolute insulin deficiency. It is the second most common chronic disease of children. By contrast, type 2 diabetes (non-insulin-dependent diabetes mellitus, NIDDM) is characterized by insulin-resistance and Inadequate insulin secretion. A significant fraction of individuals originally diagnosed with type 2 diabetes evolve with time to a type 1 state, which is defined as exhibiting anti-β-cell autoimmunity.

Because genetic factors contribute to the development of diabetes, the disease displays a strong familial aggregation. Although there are monogenic syndromes of insulin resistance, in which a definite gene has been identified as the cause of insulin resistance, these are relative rare. The more common presentation of diabetes appears to be polygenic. Additionally, behavioural- and lifestyle-related risk factors exist. Type 2 diabetes is Increasingly common primarily because of increases in the prevalence of a sedentary lifestyle and obesity. One of the major arguments for the role of behavioural factors in the etiology of diabetes has been the rapid increase in the prevalence and incidence of the disease in populations undergoing rapid westernization. The westernization transition is usually accompanied by increases in obesity, decreases in physical activity and alterations in dietary intake toward more calories, fat and non-complex carbohydrates.

Plasma glucose concentrations are normally maintained within a fairly narrow range despite wide fluctuations in the body's supply (e.g. meals) and demand (e.g. exercise) for nutrients. After an overnight fast, insulin-independent tissues, the brain (50%) and splanchnic organs (25%), account for most of the total body glucose disposal. Insulin-dependent tissues, adipose tissue and primarily skeletal muscles, are responsible for the remaining 25% of glucose utilization. This basal glucose uptake is precisely matched by the release of glucose from the liver. In response to hyperglycemia after a meal, pancreatic insulin secretion is stimulated and the combination of hyperinsulinemia plus hyperglycemia promotes glucose uptake (by splanchnic and peripheral, primarily muscle, tissues) and suppresses hepatic glucose production. It follows, therefore, that defects at the level of the β-cell, muscle and liver can lead to the development of glucose intolerance and diabetes mellitus. All the abnormalities in diabetes basically result from an imbalance between insulin sensitivity and insulin secretion. The initial stage of diabetes is characterised by impaired glucose tolerance and postprandial hyperglycemia. As the disease progresses, fasting hyperglycemia is observed.

The earliest detectable abnormality in NIDDM is an impairment in the body's ability to respond to insulin. Because the pancreas is able to appropriately augment its secretion of insulin to offset the insulin resistance, glucose tolerance remains normal. With time, however, the beta-cell fails to maintain its high rate of insulin secretion and the insulin resistance leads to the development of impaired glucose tolerance and eventually overt diabetes mellitus. The cause of pancreatic "exhaustion" remains unknown. Insulin resistance in NIDDM involves both hepatic and peripheral tissues. In response to both endogenously secreted or exogenously administered insulin, hepatic glucose production fails to suppress normally and muscle glucose uptake is diminished. The accelerated rate of hepatic glucose output is due mainly to augmented gluconeogenesis. In muscle many cellular defects in insulin action have been described including impaired insulin-receptor tyrosine kinase activity, diminished glucose transport, and reduced glycogen synthase and pyruvate dehydrogenase activities. The abnormalities account for disturbances in the two major intracellular pathways of glucose disposal, glycogen synthesis and glucose oxidation. In the earliest stages of NIDDM, the major defect involves the inability of insulin to promote glucose uptake and storage as glycogen. Other potential mechanisms that have been put forward to explain the glucose intolerance include increased levels of free fatty acids, chronic low-grade activation of the immune system (increased levels of TNFα and IL6), altered skeletal muscle blood flow, increased conversion of amylin to its insoluble amyloid form and glucose toxicity.

Diabetes is associated with a variety of physiologic disorders such as hypertension and dyslipidemia. Diabetes also increases the risk of macrovascular (coronary artery disease, stroke, amputation) and microvascular (blindness, renal failure, neuropathies) diseases. Myocardial infarction, stroke or renal failure are the cause of death for more than 70% of diabetes patients. The huge mortality and debilitating neuropathies associated with diabetes underline the importance of active medical intervention.

There are several ways to counteract diabetes. The first is lifestyle adjustments aimed at improving endogenous insulin sensitivity. This can be achieved by increased physical activity and bodyweight reduction with diet and behavioural modification. Unfortunately, most people with non-insulin-dependent diabetes mellitus never receive sufficient nutritional education or are not capable of complying with a strict diet regimen.

Another therapeutic way involves increasing insulin availability by the administration of exogenous insulin, insulin analogues and insulin secretagogues such as sulphonylureas. The primary mode of action of sulphonylureas is through the depolarisation of the pancreatic β-cells by blocking the ATP-dependent potassium channels and causing an influx of calcium ions, which stimulate insulin secretion. The most frequently encountered adverse effect of insulin, insulin analogues and insulin secretagogues is hypoglycemia. Bodyweight gain can also be a concern, because insulin not only increases uptake of blood glucose but also promotes the synthesis and storage of lipids.

Biguanides, of which metformin is the most commonly used, also have proven to be effective anti-hyperglycemic agents. Metformin reduces hepatic gluconeogenesis and basal hepatic glucose output. Its most serious adverse effect is lactic acidosis. Other common adverse effects of metformin are nausea and anorexia. Oral antidiabetics such as sulphonylureas and metformin as monotherapy or in combination have been shown to decrease fasting plasma glucose levels, but postprandial hyperglycemia persists in more than 60% of patients and probably accounts for sustained increases of hemoglobin $A_{1c}$ levels.

α-Glucosidase inhibitors, e.g. acarbose and miglitol, primarily target postprandial hyperglycemia. The therapy of diabetes mellitus with α-glucosidase inhibitors is based on a delayed intestinal degradation of starch and sucrose. These carbohydrates must be hydrolysed by α-glucosidases to monosaccharides before they can be transported through the mucosa of the small intestine. The reversible inhibition of the brush border glucosidases results in redistribution of carbohydrate absorption from the upper portion of the gut to a more extended surface area covering the whole length of the small intestine. This is accompanied by a delayed absorption of monosaccharides and a decrease in the postprandial elevation of blood glucose. Common adverse effects of α-Glucosidase inhibitors are symptoms of carbohydrate malabsorption and gastrointestinal discomfort.

Another class of antidiabetic drugs are thiazolidinediones, such as rosiglitazone and pioglitazone, which are insulin sensitizers and act through activation of peroxisome proliferator-activated receptor γ (PPARγ). PPARγ is mainly expressed in adipose tissues, plays an important role in adipogenesis and modifies fatty acid synthesis and storage. Binding of rosiglitazone to PPARγ results in reduced endogenous glucose production and increased blood glucose uptake. It increases the sensitivity of skeletal muscle, liver and adipose tissues to insulin. Improvements in glucose metabolism with rosiglitazone treatment are closely correlated with decreased plasma free fatty acid metabolism. The stimulation by rosiglitazone of PPARγ in adipose tissue and subsequent adipocyte differentiation results in the generation of more, but smaller, adipocytes which are more insulin sensitive and produce less free fatty acid, TNFα and leptin. Common adverse effects of rosiglitazone are anemia, oedema and increased body weight.

DESCRIPTION OF THE INVENTION

It is therefore the object of the present invention to make available a preparation for the treatment of diabetes mellitus which overcomes the abovementioned disadvantages.

The object on which the invention is based is surprisingly achieved by the use of certain known PDE4 inhibitors.

The expression "PDE4 inhibitor" as used herein means a compound that only or essentially only inhibits the PDE4 enzyme, not a compound which Inhibits to a degree of exhibiting a therapeutic effect also other members of the PDE enzyme family.

PDE4 inhibitors that may be usefully employed in the present invention are those which are named expressis verbis as an example or are described and/or claimed generically in the following patent applications or patents [hereinafter referred to as SELECTED PDE4 INHIBITORs]: WO9501338, WO9603399, WO9636625, WO9636626, WO9728131, WO9735854, WO9807715, WO9808841, WO9821207, WO9821209, WO9831674, WO9905111, WO9905112, WO9905113, WO9931071, WO9931090, WO9957115, WO9964414, WO0001695, WO0042017, WO0042018, WO0042019, WO0042020, WO0042034, WO0130766, WO0130777, WO0151470, WO0205616, WO0206238, WO0206239, WO0206270, WO02064584, WO02085885, WO2004/017974, WO2004/018449, WO2004/018450, WO2004/01857, WO2004/019944 and WO2004/019945.

One group of PDE4 inhibitors that may be preferably employed in the present invention [hereinafter referred to as "SELECTED PDE4 INHIBITORS—EMBODIMENT A"] includes a compound of formula 1

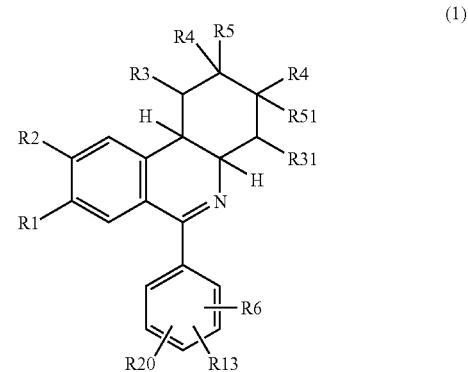

in which

R1 is hydroxyl, 1-4C-alkoxy, 3-7C-cycloalkoxy, 3-7C-cycloalkylmethoxy or completely or predominantly fluorine-substituted 1-4C-alkoxy, R2 is hydroxyl, 1-4C-alkoxy, 3-7C-cycloalkoxy, 3-7C-cycloalkylmethoxy or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, or in which R3 and R31 together are a 1-4C-alkylene group, R4 is hydrogen or 1-4C-alkyl,
R5 is hydrogen,
R51 is hydrogen,
or in which
R5 and R51 together represent an additional bond,
R6 is O—R7, S—R8, C(O)—R9, CH$_2$—R10, S(O)$_2$-aryl, O—S(O)$_2$—R11, pyrrolidin-1-yl, pyrrolidin-1-yl-2-one, pyrrolidin-1-yl-2,5-dione, piperidin-1-yl, piperidin-1-yl-2-one or piperidin-1-yl-2,6-dione, where
R7 is 3-7C-cycloalkyl, 3-7C-cycloalkylmethyl, 1-4C-alkoxy-1-4C-alkyl, aryl or phenyl-1-4C-alkyl,
R8 is hydrogen, 1-4C-alkyl, 1-4C-alkylcarbonyl, arylcarbonyl, trifluoromethyl, difluoromethyl, trichloromethyl or phenyl,
R9 is 1-4C-alkyl, 3-7C-cycloalkyl, 3-7C-cycloalkylmethyl, 1-pyrrolidinyl, 1-piperidinyl, 1-piperazinyl, 4-methylpiperazinyl, 4-morpholinyl or aryl,
R10 is hydroxyl, halogen, cyano, carboxyl, 1-4C-alkoxy, phenoxy, 1-4C-alkoxycarbonyl, aminocarbonyl, mono- or di-1-4C-alkylaminocarbonyl, N(R15)R16 or 1-4C-alkylcarbonylamino, and
R11 is 1-4C-alkyl, amino, mono- or di-1-4C-alkylamino or aryl,
aryl is phenyl, pyridyl or R12-substituted phenyl, where
R12 is hydroxyl, halogen, carboxyl, nitro, amino, cyano, 1-4C-alkyl, trifluoromethyl, 1-4C-alkoxy, 1-4C-alkoxycarbonyl, 1-4C-alkylcarbonylamino, 1-4C-alkylcarbonyloxy or aminocarbonyl,
R13 is hydrogen, hydroxyl, halogen, cyano, nitro, amino, 1-4C-alkyl, trifluoromethyl, 1-4C-alkoxy, completely or predominantly fluorine-substituted 1-4C-alkoxy, phenyl, phenyl-1-4C-alkyl, C(O)—OR14, C(O)—N(R15)R16, N(R17)R18, S(O)$_2$—R19, S(O)$_2$—N(R15)R16 or has one of the meanings of R6, where
R14 is hydrogen, 1-4C-alkyl, 3-7C-cycloalkyl or 3-7C-cycloalkylmethyl,
R15 is hydrogen, 1-4C-alkyl, 3-7C-cycloalkyl or 3-7C-cycloalkylmethyl,
R16 is hydrogen, 1-4C-alkyl, 3-7C-cycloalkyl, 3-7C-cycloalkylmethyl or aryl, or where R15 and R16, together and including the nitrogen atom to which both are bonded, represent a 1-pyrrolidinyl, 1-piperidinyl, 1-piperazinyl, 4methylpiperazin-1-yl, 1-hexahydroazepinyl or 4-morpholinyl radical,
R17 is hydrogen, 1-4C-alkyl, S(O)$_2$—R19 or S(O)$_2$-aryl,
R18 is 1-4C-alkyl, 1-4C-alkylcarbonyl, 3-7C-cycloalkylcarbonyl, 3-7C-cycloalkylmethylcarbonyl, S(O)$_2$—R19 or S(O)$_1$-aryl, and
R19 is 1-4C-alkyl,
R20 is hydrogen, hydroxyl, halogen, nitro, amino, 1-4C-alkyl, trifluoromethyl, 1-4C-alkoxy, completely or predominantly fluorine-substituted 1-4C-alkoxy, 3-7C-cycloalkoxy, 3-7C-cycloalkyl methoxy, CH$_2$—R10, carboxyl, 1-4C-alkoxycarbonyl, 1-4C-alkylcarbonyloxy, 1-4C-alkylcarbonylamino or aminocarbonyl,
or a pharmaceutically acceptable salt or a N-Oxide thereof or a pharmaceutically acceptable salt of the latter.
SELECTED PDE4 INHIBITORs—EMBODIMENT A, which are to be emphasized include a compound of formula 1, in which
R1 is 1-2C-alkoxy,
R2 is 1-2C-alkoxy,
R3, R31, R4, R5 and R51 are hydrogen,
R6 is O—R7, S—R8, C(O)—R9, CH$_2$—R10, S(O)$_2$-phenyl, O—S(O)$_2$—R11, pyrrolidin-1-yl or pyrrolidin-1-yl-2-one, where
R7 is cyclobutyl, cyclopentyl, cyclopropylmethyl, 2-methoxyethyl, phenyl, 4-methoxyphenyl, benzyl, phenethyl or pyridyl,
R8 is phenyl,
R9 is methyl, ethyl, isobutyl, cyclopropylmethyl, 1-piperidinyl or aryl,
R10 is methoxycarbonyl, morpholin-4-yl or 1-methylpiperazin4-yl, and
R11 is methyl or 4-methylphenyl,
aryl is phenyl, pyridyl or R12-substituted phenyl, in which
R12 is methoxy, halogen, nitro or cyano,
and in which either
R13 is hydrogen, methoxy, ethoxy, difluoromethoxy or acetylamino and
R20 is hydrogen,
or
R13 is hydrogen and
R20 is cyclopropylmethoxy,
or a pharmaceutically acceptable salt or a N-Oxide thereof or a pharmaceutically acceptable salt of the latter.
SELECTED PDE4 INHIBITORs—EMBODIMENT A, which are particularly to be emphasized include a compound selected from
(−)-cis-8,9-Dimethoxy-6-(4-benzoylphenyl)-1,2,3,4,4a,10b-hexahydrophenanthridine;
(−)-cis-8,9-Dimethoxy-6-(4-acetophenyl)-1,2,3,4, 4a,10b-hexahydrophenanthridine;
(−)-cis-8,9-Dimethoxy-6-(3-benzoylphenyl)-1,2,3,4,4a,10b-hexahydrophenanthridine;
(−)-cis-8,9-Dimethoxy-6-(4-phenoxyphenyl)-1,2,3,4,4a,10b-hexahydrophenanthridine;
(−)-cis-8,9-Dimethoxy-6-(3-phenoxyphenyl)-1,2,3,4,4a,10b-hexahydrophenanthridine;
(−)-cis-8,9-Dimethoxy-6-[3-(phenylthio)phenyl]-1,2,3,4,4a,10b-hexahydrophenanthridine;
(−)-cis-8,9-Dimethoxy-6-(3-benzyloxyphenyl)-1,2,3,4,4a,10b-hexahydrophenanthridine;
(−)-cis-8,9-Dimethoxy-4-(3-phenethyloxyphenyl)-1,2,3,4,4a,10b-hexahydrophenanthridine;
(−)-cis-6-(3-Cyclopentyloxy-4-methoxyphenyl)-8,9-dimethoxy-1,2,3,4,4a,10b-hexahydrophenanthridine;
(−)-cis-6-(4-Benzyloxy-3-cyclopropylmethoxyphenyl)-8,9-dimethoxy-1,2,3,4,4a,10b-hexahydrophenanthridine;
(+)-cis-6-(3-Benzyloxy4-methoxyphenyl)-8,9-dimethoxy-1,2,3,4,4a,10b-hexahydrophenanthridine;
(−)-cis-8,9-Dimethoxy-6-[3-cyclopropylmethoxy-4-methoxyphenyl]-1,2,3,4,4a,10b-hexahydrophenanthridine;
(−)-cis-8,9-Dimethoxy-6-(3-methanesulfonyloxyphenyl)-1,2,3,4,4a,10b-hexahydrophenanthridine;
(−)-cis-8,9-Dimethoxy-6-[3-(p-toluenesulfonyloxy)phenyl]-1,2,3,4,4a,10b-hexahydrophenanthridine;
(−)-cis -8,9-Dimethoxy-6-[3,4-bis-(cyclopropylmethoxy)phenyl]-1,2,3,4,4a,10b-hexahydrophenanthridine;
(−)-cis-8,9-Dimethoxy-[4-(piperidin-1-ylcarbonyl)phenyl]-1,2,3,4,4a,10b-hexahydrophenanthridine;
(−)-cis-8,9-Dimethoxy-[3-(piperidin-1-ylcarbonyl)phenyl]-1,2,3,4,4a,10b-hexahydrophenanthridine;
(−)-cis-8,9-Dimethoxy-6-(4-methoxycarbonylmethylphenyl)-1,2,3,4,4a,10b-hexahydrophenanthridine;
cis-6-(4-Chloromethylphenyl)-9-ethoxy-8-methoxy-1,2,3,4,4a,10b-hexahydrophenanthridine;
(−)-cis-6-(4-Chloromethylphenyl)-8,9-dimethoxy-1,2,3,4,4a,10b-hexahydrophenanthridine;
(−)-cis-8,9-Dimethoxy-4-6-[4-(morpholin-4-ylmethyl)phenyl]-1,2,3,4,4a,10b-hexahydrophenanthridine;
(−)-cis-8,9-Dimethoxy-6-[4-(4-methylpiperazin-1-ylmethyl)phenyl]-1,2,3,4,4a,10b-hexahydrophenanthridine;

(−)-cis-8,9-Dimethoxy-6-[4-(3-methylbutyryl)phenyl]-1,2,3,4,4a,10b-hexahydrophenanthridine;
(−)-cis-8,9-Dimethoxy-6-[4-cyclopropylmethylcarbonylphenyl]-1,2,3,4,4a,10b-hexahydrophenanthridine;
(−)-cis-9-Ethoxy-8-methoxy-6-(4-benzoylphenyl)-1,2,3,4,4a,10b-hexahydrophenanthridine;
(−)-cis-8,9-Dimethoxy-6-[4-(4-methoxybenzoyl)phenyl]-1,2,3,4,4a,10b-hexahydrophenanthridine;
(−)-cis-8,9-Dimethoxy-6-[4-(4-chlorbenzoyl)phenyl]-1,2,3,4,4a,10b-hexahydrophenanthridine;
(−)-cis-8,9-Dimethoxy-6-[4-(3-chlorbenzoyl)phenyl]-1,2,3,4,4a,10b-hexahydrophenanthridine;
(−)-cis-8,9-Dimethoxy-6-[4-(4-nitrobenzoyl)phenyl]-1,2,3,4,4a,10b-hexahydrophenanthridine;
(−)-cis-8,9-Dimethoxy-6-[4-(3-methoxybenzoyl)phenyl]-1,2,3,4,4a,10b-hexahydrophenanthridine;
(−)-cis-8,9-Dimethoxy-6-[4-(4-cyanobenzoyl)phenyl]-1,2,3,4,4a,10b-hexahydrophenanthridine;
(−)-cis-8,9-Dimethoxy-6-[4-(pyridyl-4-carbonyl)phenyl]-1,2,3,4,4a,10b-hexahydrophenanthridine;
(−)-cis-8,9-Dimethoxy-6-[3-(phenylsulfonyl)phenyl]-1,2,3,4,4a,10b-hexahydrophenanthridine;
(−)-cis-8,9-Dimethoxy-6-[4-(phenylsulfonyl)phenyl]-1,2,3,4,4a,10b-hexahydrophenanthridine;
(−)-cis 8,9-Dimethoxy-6-(3-cyclopropylmethoxyphenyl)-1,2,3,4,4a,10b-hexahydrophenanthridine;
(−)-cis-8,9-Dimethoxy-6-[3-(4-methoxyphenoxy)phenyl]-1,2,3,4,4a,10b-hexahydrophenanthridine;
(−)-cis-8,9-Dimethoxy-6-[3-(pyrid-4-yloxy)phenyl]-1,2,3,4,4a,10b-hexahydrophenanthridine;
(−)-cis-8,9-Dimethoxy-6-(3-cyclopropylmethoxy-4-ethoxyphenyl)-1,2,3,4,4a,10b-hexahydrophenanthridine;
(−)-cis-9-Ethoxy-8-methoxy-6-[(3-cyclopropylmethoxy-4-ethoxy)phenyl]-1,2,3,4,4a,10b-hexahydrophenanthridine;
(−)-cis-9-Ethoxy-8-methoxy-6-[3,4-bis(cyclopropylmethoxy)phenyl]-1,2,3,4,4a,10b-hexahydrophenanthridine;
(−)-cis-8,9-Dimethoxy-6-[3,5-bis(cyclopropylmethoxy)phenyl]-1,2,3,4,4a,10b-hexahydrophenanthridine;
(−)-cis-8,9-Dimethoxy-6-(3-cyclopropylmethoxy-4difluoromethoxyphenyl)-1,2,3,4,4a,10b-hexahydrophenanthridine;
(−)-cis-8,9-Dimethoxy-6-[3-(2-methoxyethoxy)-4-methoxyphenyl]-1,2,3,4,4a,10b-hexahydrophenanthridine;
(−)-cis-8,9-Dimethoxy-6-[(3-cyclobutoxy-4-methoxy)phenyl]-1,2,3,4,4a,10b-hexahydrophenanthridine
(−)-cis-8,9-Dimethoxy-6-[(3-cyclopropylmethoxy-4-acetamido)phenyl]-1,2,3,4,4a,10b-hexahydrophenanthridine;
(−)-cis-8,9-Dimethoxy-6-[(4-methoxy-3-pyrrolidin-1-yl)phenyl]-1,2,3,4,4a,10b-hexahydrophenanthridine;
(−)-cis-8,9-Dimethoxy-6-[4-methoxy-3-(2-oxopyrrolidin-1-yl)phenyl]-1,2,3,4,4a,10b-hexahydrophenanthridine;
(−)-cis -,9-Dimethoxy-6-{[3-(2,5dioxopyrrolidin-1-yl)-4-methoxy]phenyl}-1,2,3,4,4a,10b-hexahydrophenanthridine;
(−)-cis-8,9-Dimethoxy-6-(3-acetylphenyl)-1,2,3,4,4a,10b-hexahydrophenanthridine and
(−)-cis-8,9-Dimethoxy-6-[4-propionylphenyl]-1,2,3,4,4a,10b-hexahydrophenanthridine;
or a pharmaceutically acceptable salt or a N-Oxide thereof or a pharmaceutically acceptable salt of the latter.

SELECTED PDE4 INHIBITORs—EMBODIMENT A, which are preferred include a compound selected from
(−)-cis-8,9-Dimethoxy-6-(4-benzoylphenyl)-1,2,3,4,4a,10 b-hexahydrophenanthridine and
(−)-cis-8,9-Dimethoxy-6-[3,4-bis-(cyclopropylmethoxy)phenyl]-1,2,3,4,4a,10b-hexahydrophenanthridine;

or a pharmaceutically acceptable salt or a N-Oxide thereof or a pharmaceutically acceptable salt of the latter.

SELECTED PDE4 INHIBITORs—EMBODIMENT A, which are particularly preferred include a compound selected from
(−)-cis-8,9-Dimethoxy-6-(4-benzoylphenyl)-1,2,3,4,4a,10b-hexahydrophenanthridine and
(−)-cis-8,9-Dimethoxy-6-[3,4-bis-(cyclopropylmethoxy)phenyl]-1,2,3,4,4a,10b-hexahydrophenanthridine;
or a pharmaceutically acceptable salt thereof.

Another group of PDE4 inhibitors that may be preferably employed in the present invention [hereinafter referred to as "SELECTED PDE4 INHIBITORs—EMBODIMENT B"] includes a compound of formula 2

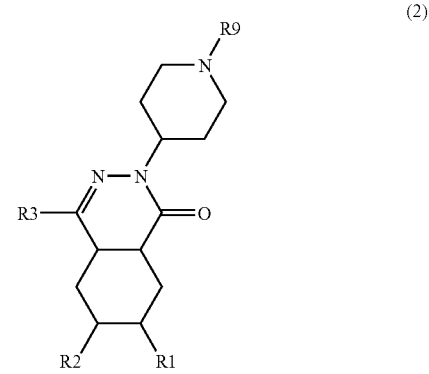

(2)

in which
R1 and R2 are both hydrogen or together form an additional bond,
R3 represents a benzene derivative of formula (a) or (b)

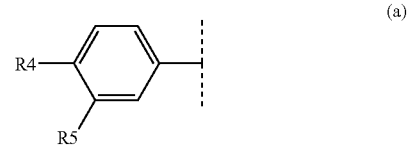

(a)

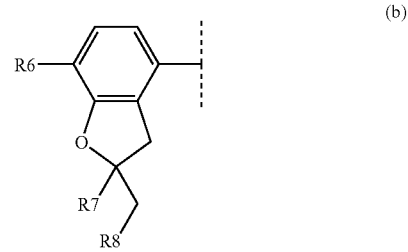

(b)

wherein
R4 is 1-4C-alkoxy or 1-4C-alkoxy which is completely or predominantly substituted by fluorine,
R5 is 1-8C-alkoxy, 3-7C-cycloalkoxy, 3-7C-cycloalkylmethoxy, or 1-4C-alkoxy which is completely or predominantly substituted by fluorine,
R6 is 1-4C-alkoxy, 3-5C-cycloalkoxy, 3-5C-cycloalkylmethoxy, or 1-4C-alkoxy which is completely or predominantly substituted by fluorine,
R7 is 1-4C-alkyl and
R8 is hydrogen or 1-4C-alkyl,
or wherein R7 and R8 together and with inclusion of the two carbon atoms, to which they are bonded, form a spiro-linked 5-, 6- or 7-membered hydrocarbon ring, optionally interrupted by an oxygen or sulphur atom, R9 is 1-4C-Alkyl, —S(O)$_2$—R10, —S(O)$_2$—(CH$_2$)$_n$—R11, —(CH$_2$)$_m$—S(O)$_2$—R12, —C(O)R13, —C(O)—(CH$_2$)$_n$—R14, —(CH$_2$)$_m$—C(O)—R15, Hetaryl, Aryl1 or Aryl2-(1-4C)-alkyl, R10 is 1-4C-alkyl, 5-dimethylaminonaphthalin-1-yl, —N(R16)R17, phenyl or phenyl substituted by R18 and/or R19, R11 is —N(R16)R17, R12 is —N(R16)R17, R13 is 1-4C-alkyl, hydroxycarbonyl-1-4C-alkyl, phenyl, pyridyl, 4-ethyl-piperazin-2,3-dion-1-yl or —N(R16)R17, R14 is —N(R16)R17, R15 is —N(R16)R17, phenyl, phenyl substituted by R18 and/or R19 and/or R20, R16 and R17 are independent from each other hydrogen, 1-7C-alkyl, 3-7C-cycloalkyl, 3-7C-cycloalkyl-methyl, phenyl or phenyl substituted by R18 and/or R19 and/or R20, or R16 and R17 together and with inclusion of the nitrogen atom to which they are bonded, form a 4-morpholinyl-, 1-pyrrolidinyl-, 1-piperidinyl-, 1-hexahydroazepino- or a 1-piperazinyl-ring of formula (c)

(c)

wherein

R21 is pyrid-4-yl, pyrid4-ylmethyl, 1-4C-alkyl-dimethylamino, dimethylaminocarbonylmethyl, N-methyl-piperidin-4-yl, 4morpholino-ethyl or tetrahydrofuran-2-ylmethyl, R18 is halogen, nitro, cyano, carboxyl, 1-4C-alkyl, trifluoromethyl, 1-4C-alkoxy, 1-4C-alkoxycarbonyl, amino, mono-or di-1-4C-alkylamino, aminocarbonyl, 1-4C-alkylcarbonylamino or mono-or di-1-4C-alkylaminocarbonyl, R19 is halogen, amino, nitro, 1-4C-alkyl or 1-4C-alkoxy, R20 is halogen, Hetaryl is pyrimidin-2-yl, thieno-[2,3d]pyrimidin-4-yl, 1-methyl-1H-pyrazolo-[3,4d]pyrimidin-4-yl, thiazolyl, imidazolyl or furanyl, Aryl1 is pyridyl, phenyl or phenyl substituted by R18 and/or R19, Aryl2 is pyridyl, phenyl, phenyl substituted by R18 and/or R19, 2oxo-2H-chromen-7-yl or 4(1,2,3-thiadiazol-4-yl) phenyl, n is an integer from 1 to 4, m is an integer from 1 to 4, or a pharmaceutically acceptable salt or a N-oxide thereof or a pharmaceutically acceptable salt of the latter.

SELECTED PDE4 INHIBITORs—EMBODIMENT B, which are to be emphasized include a compound of formula 2, in which R1 and R2 together form an additional bond, R3 represents a benzene derivative of formula (a) or (b)

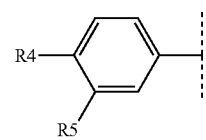

(a)

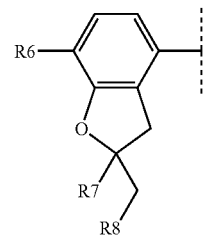

(b)

wherein

R4 is 1-4C-alkoxy,

R5 is 1-4C-alkoxy,

R6 is 1-2C-alkoxy,

R7 is methyl and

R8 is hydrogen,

R9 is 1-4C-alkyl, —S(O)$_2$R10, —C(O)R13, —C(O)—(CH$_2$)$_n$—R14, —(CH$_2$)$_m$—C(O)—R15, Hetaryl, Aryl1 or Aryl2-(1-2C-)alkyl, R10 is 1-4C-alkyl, 5-dimethylaminonaphthalin-1-yl, phenyl or phenyl substituted by R18, R13 is 1-4C-alkyl, hydroxycarbonyl-1-4C-alkyl, pyridyl, 4ethyl-piperazin-2,3-dion-1-yl or —N(R16)R17, R14 is —N(R16)R17, R15 is —N(R16)R17, phenyl or phenyl substituted by R18 and/or R19 and/or R20, R16 and R17 are independent from each other hydrogen, 1-4C-alkyl, phenyl or phenyl substituted by R18 and/or R19 and/or R20, or R16 and R17 together and with inclusion of the nitrogen atom to which they are bonded, form a 4-morpholinyl ring or a 1-piperazinyl ring of formula (c)

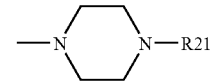

(c)

wherein

R21 is dimethylamino-1-4C-alkyl,

R18 is halogen, nitro, 1-4C-alkyl or 1-4C-alkoxycarbonyl,

R19 is amino,

R20 is halogen,

Hetaryl is pyrimidin-2-yl, thieno-[2,3-d]pyrimidin-4-yl or 1-methyl-1H-pyrazolo-[3,4-]pyrimidin-4-yl, Aryl1 is phenyl or phenyl substituted by R18, Aryl2 is pyridyl, phenyl, 2-oxo-2H-chromen-7-yl or 4(1,2,3-thiadiazol-4-yl)phenyl, n is1 or2, m is 1 or 2, or a pharmaceutically acceptable salt or a N-oxide thereof or a pharmaceutically acceptable salt of the latter.

SELECTED PDE4 INHIBITORs—EMBODIMENT B, which are particularly to be emphasized include a compound selected from (4aS,8aR)-4-(3,4-Diethoxyphenyl)-2-[1-(toluene-4-sulfonyl)-piperidin-4-yl]-4a,5,8,8a-tetrahydro-2H-phthalazin-1-one, (4aS,8aR)-4-(3,4-Diethoxyphenyl)-2-(1-methanesulfonyl-piperidin-4-yl)-4a,5,8,8a-tetrahydro-2H-phthalazin-1-one, (4aS,8aR)-2-(1-Acetyl-piperidin-4-yl)-4-(3,4-diethoxyphenyl)-4a,5,8,8a-tetrahydro-2H-phthalazin-1-one, 5-{4-[(4aS,8aR)-4-(3,4-Diethoxy-phenyl)-1-oxo-4a,5,8,8a-tetrahydro-1H-phthalazin-2-yl]-piperidin-1-yl}-5-oxo-pentanoic acid, (4aS,8aR)-4-(3,4-Diethoxyphenyl)-2-[1-(1-pyridin-4-yl-methanoyl)-piperidin-4yl]4a,5,8,8a-tetrahydro-2H-phthalazin-1-one, 4-[(4aS,8aR)-4-(3,4-Diethoxyphenyl)-1-oxo-4a,5,8,8a-tetrahydro-1H-phthalazin-2-yl]-piperidine-1-carboxylic acid tert-butylamide, 4-[(4aS,8aR)-4-(3,4-Diethoxyphenyl)-1-oxo-4a,5,8,8a-tetrahydro-1H-phthalazin-2-yl]-piperidine-1-carboxylic acid phenylamide, 4-[(4aS,8aR)4-(3,4-Dimethoxyphenyl)-1-oxo-4a,5,8,8a-tetrahydro-1H-phthalazin-2-yl]-piperidine-1-carboxylic acid tert-butylamide, (cis)-4-[4-(7-Methoxy-2,2-dimethyl-2,3-dihydro-benzofuran-4-yl)-1-oxo-4a,5,8,8a-tetrahydro-1H-phthalazin-2-yl]-piperidine-1-carboxylic acid tert-butylamide, (4aS,8aR)-4-(3,4-Dimethoxyphenyl)-2-[1-(5-dimethylamino-naphthalene-1-sulfonyl)-piperidin-4-yl]-4a,5,8,8a-tetrahydro-2H-phthalazin-1-one, (4aS,8aR)-4-(3,4-Dimethoxyphenyl)-2-[1-(4-nitro-phenyl)-piperidin-4-yl]-4a,5,8,8a-tetrahydro-2H-phthalazin-1-one, (4aS,8aR)-4-(3,4-Dimethoxyphenyl)-2-(1-pyridin-4-ylmethyl-piperidin-4-yl)-4a,5,8,8a-tetrahydro-2H-phthalazin-1-one, (4aS,8aR)-4-(3,4-Dimethoxyphenyl)-2-[1-(morpholine-4-carbonyl)-piperidin-4-yl]-4a,5,8,8a-tetrahydro-2H-phthalazin-1-one, (4aS,8aR)-2-{1-[2-(4-Amino-3,5-dichloro-phenyl)-2-oxo-ethyl]-piperidin-4yl}-4-(3,4-dimethoxy-phenyl)-4a,5,8,8a-tetrahydro-2H-phthalazin-1-one, 4-(3,4-Dimethoxyphenyl)-2-[1-(1-methyl-1H-pyrazolo[3,4d]pyrimidin-4-yl)-piperidin-4-yl]-4a,5,8,8a-tetrahydro-2H-naphthalen-1-one, (4aS,8aR)-4-(3,4-Dimethoxyphenyl)-2-(1-thieno[2,3d]pyrimidin-4-yl-piperidin-4-yl)-4a,4,8,8a-tetrahydro-2H-phthalazin-1-one, (4aS,8aR)-4-(3,4-Dimethoxyphenyl)-2-(1-pyrimidin-2-yl-piperidin-4-yl)-4a,5,8,8a-tetrahydro-2H-phthalazin-1-one, (4aS,8aR)-4-(3,4-Dimethoxyphenyl)-2-[1-(2-oxo-2H-chromen-7-ylmethyl)-piperidin-4-yl]-4a,5,8,8a-tetrahydro-2H-phthalazin-1-one, 4-(3,4-Dimethoxyphenyl)-2-(1-isopropyl-piperidin-4-yl)-4a,5,8,8a-tetrahydro-2H-phthalazin-1-one, (4aS,8aR)-4-(3,4-Dimethoxyphenyl)-2-[1-(2-morpholin-4-yl-2-oxo-ethyl)-piperidin-4-yl]-4a,5,8,8a-tetrahydro-2H-phthalazin-1-one, (4aS,8aR)-4-(3,4-Dimethoxyphenyl)-2-(1-phenethyl-piperidin-4-yl)-4a,5,8,8a-tetrahydro-2H-phthalazin-1-one, (4aS,8aR)-4-(3,4-Diethoxyphenyl)-2-[1-(morpholine-4-carbonyl)-piperidin-4-yl]-4a,5,8,8a-tetrahydro-2H-phthalazin-1-one, (4aS,8aR)-4-(3,4-Dimethoxyphenyl)-2-(1-pyridin-3-ylmethyl-piperidin-4-yl)4a,5,8,8a-tetrahydro-2H-phthalazin-1-one, (4aS,8aR)-4-(3,4-Dimethoxy-phenyl)-2-(1-pyridin-2-ylmethyl-piperidin-4-yl)-4a,5,8,8a-tetrahydro-2H-phthalazin-1-one, (4aS,8aR)-4-(3,4-Diethoxyphenyl)-2-[1-(2-morpholin-4-yl-ethanoyl)-piperidin-4-yl]-4a,5,8,8a-tetrahydro-2H-phthalazin-1-one, (4aS,8aR)-4-(3,4-Diethoxyphenyl)-2-(1-{2-[4-(2-dimethylamino-ethyl)-piperazin-1-yl]-ethanoyl}-piperidin-4-yl)-4a,5,8,8a-tetrahydro-2H-phthalazin-1-one, 2-{4-[(4aS,8aR)-4-(3,4-Dimethoxyphenyl)-1-oxo-4a,5,8,8a-tetrahydro-1H-phthalazin-2-yl]-piperidin-1-yl}-N-isopropyl-acetamide, (4aS,8aR)-4-(3,4-Dimethoxyphenyl)-2-[1-(4-1,2,3-thiadiazol-4-yl-benzyl)-piperidin-4-yl]-4a,5,8,8a-tetrahydro-2H-phthalazin-1-one, 1-(1-{4-[(4aS,8aR)-4-(3,4-Dimethoxyphenyl)-1-oxo-4a,5,8,8a-tetrahydro-1H-phthalazin-2-yl]-piperidin-1yl}-methanoyl)-4-ethyl-piperazine-2,3-dione, 4-(2-{4-[(4aS,8aR)-4-(3,4-Dimethoxy-phenyl)-1-oxo-4a,5,8,8a-tetrahydro-1H-phthalazin-2-yl]-piperidin-1yl}-ethanoylamino)-benzoic acid ethyl ester and 2-{4-[(4aS,8aR)-4-(3,4-Dimethoxyphenyl)-1-oxo-4a,5,8,8a-tetrahydro-1H-phthalazin-2-yl]-piperidin-1-yl}-acetamide, or a pharmaceutically acceptable salt or a N-oxide thereof or a pharmaceutically acceptable salt of the latter.

SELECTED PDE4 INHIBITORs—EMBODIMENT B, which are preferred include a compound selected from (4aS,8aR)-4-(3,4-Dimethoxyphenyl)-2-(1-pyrimidin-2-yl-piperidin-4-yl)-4a,5,8,8a-tetrahydro-2H-phthalazin-1-one, (4aS,8aR)-4-(3,4-Dimethoxy-phenyl)-2-(1-pyridin-2-ylmethyl-piperidin-4-yl)-4a,5,8,8a-tetrahydro-2H-phthalazin-1-one, 2-{4-[(4aS,8aR)-4-(3,4-Dimethoxyphenyl)-1-oxo-4a,5,8,8a-tetrahydro-1H-phthalazin-2-yl]-piperidin-1-yl}-acetamide, or a pharmaceutically acceptable salt or a N-oxide thereof or a pharmaceutically acceptable salt of the latter.

SELECTED PDE4 INHIBITORs—EMBODIMENT B, which are particularly preferred include a compound selected from (4aS,8aR)-4-(3,4-Dimethoxyphenyl)-2-(1-pyrimidin-2-yl-piperidin-4-yl)4a,5,8,8a-tetrahydro-2H-phthalazin-1-one, (4aS,8aR)-4-(3,4-Dimethoxy-phenyl)-2-(1-pyridin-2-ylmethyl-piperidin-4-yl)-4a,5,8,8-tetrahydro-2H-phthalazin-1-one, 2-{4-[(4aS,8aR)-4-(3,4-Dimethoxyphenyl)-1-oxo-4a,5,8,8a-tetrahydro-1H-phthalazin-2-yl]-piperidin-1yl}-acetamide, or a pharmaceutically acceptable salt thereof.

A further group of PDE4 inhibitors that may be preferably employed in the present invention [hereinafter referred to as "SELECTED PDE4 INHIBITORs—Embodiment C"] include a compound selected from (+)-cis-8,9-Dimethoxy-6-(4-carboxyphenyl)-1,2,3,4,4a,10b-hexahydrophenanthridine and (−)-cis-6-[4-(2-Ethyl-2H-tetrazol-5-yl)-phenyl]-8,9-dimethoxy-1,2,3,4,4a,10b-hexahydrophenanthridine or a pharmaceutically acceptable salt or a N-Oxide thereof or a pharmaceutically acceptable salt of the latter.

Particularly preferred SELECTED PDE4 INHIBITORs—EMBODIMENT C include a compound selected from (+)-cis-8,9-Dimethoxy-6-(4-carboxyphenyl)-1,2,3,4,4a,10b-hexahydrophenanthridine and (−)-cis-6-[4-(2-Ethyl-2H-tetrazol-5-yl)-phenyl]-8,9-dimethoxy-1,2,3,4,4a,10b-hexahydrophenanthridine or a pharmaceutically acceptable salt thereof.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1-8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1-4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms are replaced by fluorine atoms.

As spiro-linked 5-, 6- or 7-membered hydrocarbon rings, optionally interrupted by an oxygen or sulphur atom in the compounds of formula 2, may be mentioned the cyclopentane, cyclohexane, cycloheptane, tetrahydrofuran, tetrahydropyran and the tetrahydrothiophen ring.

1-2C-Alkylenedioxy represents, for example, the methylenedioxy [—O—CH$_2$—O—] and the ethylenedioxy [—O—CH$_2$—CH$_2$—O—] radicals.

If R3 and R31 in the compounds of formula 1 together have the meaning 1-4C-alkylene, the positions 1 and 4 in compounds of the formula I are linked to one another by a 1-4C-alkylene bridge, 1-4C-alkylene representing straight-chain or branched alkylene radicals having 1 to 4 carbon atoms. Examples which may be mentioned are the radicals methylene [—CH$_2$—], ethylene [—CH$_2$—CH$_2$], trimethylene [—CH$_2$—CH$_2$—CH$_2$—], 1,2-dimethylethylene [—CH(CH$_3$)—CH(CH$_3$)—] and isopropylidene [—C(CH$_3$)$_2$—].

If R5 and R51 in the compounds of formula 1 together are an additional bond, then the carbon atoms in positions 2 and 3 in compounds of the formula I are linked to one another via a double bond.

Halogen within the meaning of the invention is bromine, chlorine or fluorine.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkylmethyl represents a methyl radical which is substituted by one of the abovementioned 3-7C-cycloalkyl radicals. Preferably, the 3-5C-cycloalkylmethyl radicals cyclopropylmethyl, cyclobutylmethyl and cyclopentylmethyl may be mentioned.

1-4C-Alkoxy-1-4C-alkyl represents one of the abovementioned 1-4C-alkyl radicals, which is substituted by one of the abovementioned 1-4C-alkoxy radicals. Examples which may be mentioned are the methoxymethyl, the methoxyethyl and the isopropoxyethyl radicals.

Phenyl-1-4C-alkyl represents one of the abovementioned, phenyl-substituted 1-4C-alkyl radicals. Examples which may be mentioned are the phenethyl and the benzyl radicals.

1-4C-Alkylcarbonyl represents a radical which, in addition to the carbonyl group, contains one of the abovementioned 1-4C-alkyl radicals. An example which may be mentioned is the acetyl radical.

3-7C-Cycloalkylcarbonyl represents a radical which, in addition to the carbonyl group, contains one of the abovementioned 3-7C-cycloalkyl radicals. An example which may be mentioned is the cyclopentylcarbonyl radical.

3-7C-Cycloalkylmethylcarbonyl represents a radical which, in addition to the carbonyl group, contains one of the abovementioned 3-7C-cycloalkylmethyl radicals. An example which may be mentioned is the cyclopropylmethylcarbonyl radical.

1-4C-Alkoxycarbonyl represents a carbonyl group to which one of the abovementioned 1-4C-alkoxy radicals is bonded. Examples which may be mentioned are the methoxycarbonyl [CH$_3$—O—C(O)—] and the ethoxycarbonyl [CH$_3$CH$_2$O—C(O)—] radicals.

1-4C-Alkylcarbonyloxy represents a carbonyloxy group to which one of the abovementioned 1-4C-alkyl radicals is bonded. An example which may be mentioned is the acetoxy radical [CH$_3$C(O)—O—].

In addition to the carbonyl group, mono- or di-1-4C-alkylaminocarbonyl radicals contain one of the abovementioned mono- or di-1-4C-alkylamino radicals. Examples which may be mentioned are the N-methyl-, the N,N-dimethyl-, the N-ethyl-, the N-propyl-, the N,N-diethyl- and the N-isopropylaminocarbonyl radicals.

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

As a 1-4C-alkylcarbonylamino radical, for example, the propionylamino [C$_3$H$_7$C(O)NH—] and the acetylamino [CH$_3$C(O)NH—] radicals may be mentioned.

Exemplary phenyl radicals substituted by R6, R13 and R20 in the compounds of formula 1 which may be mentioned are 3-phenoxyphenyl, 4-phenoxyphenyl, 3-benzyloxyphenyl, 4-benzyloxyphenyl, 3-phenethoxyphenyl, 4-phenethoxyphenyl, 3-benzyloxy-4-methoxyphenyl, 4-benzyloxy-3-methoxyphenyl, 3-benzyloxy-5-methoxyphenyl, 4-benzyloxy-3-cyclopropylmethoxyphenyl, 3-cyclopentyloxyphenyl, 4-cyclopentyloxyphenyl, 4-cyclohexyloxyphenyl, 3-cyclohexyloxyphenyl, 3-cyclopropylmethoxyphenyl, 4-cyclopropylmethoxyphenyl, 3-cyclopropylmethoxy-4-methoxyphenyl, 3-cyclopropylmethoxy-4-difluoromethoxyphenyl, 3-cyclopropylmethoxy-4-ethoxyphenyl, 4-cyclopropylmethoxy-3-methoxyphenyl, 3-cyclopropylmethoxy-5-methoxyphenyl, bis-3,4-cyclopropylmethoxyphenyl, bis-3,5-cyclopropylmethoxyphenyl, 3,4-dicyclopentyloxyphenyl, 3-cyclopentyloxy-4-methoxyphenyl, 4-cyclopentyloxy-3- methoxyphenyl, 3-cyclopropylmethoxy-4-cyclopentyloxyphenyl, 3-cyclopentyloxy-5methoxyphenyl, 4cyclopropylmethoxy-3-cyclopentyloxyphenyl, 3-cyclobutyloxy-4-methoxyphenyl, 4-(3-hydroxyphenoxy)phenyl, 4-(4-hydroxyphenoxy)phenyl, 3-methoxyethoxy-4-methoxyphenyl, 3-cyclopropylmethoxy-4-acetylaminophenyl, 4-mercaptophenyl, 4-ethylthiophenyl, 2-methylthiophenyl, 4-methylthiophenyl, 4-trifluoromethylthiophenyl, 4-methylthio-3-nitrophenyl, 4-phenylthiophenyl, 3-phenylthiophenyl, 2-methoxy-4-methylthiophenyl, 4-[(4-chlorophenyl)thio]-3-nitrophenyl, 3-methylsulfonyloxyphenyl, 4-methylsulfonyloxyphenyl, 3-(p-toluenesulfonyloxy)phenyl, 4-(p-toluenesulfonyloxy)phenyl, 4-[(4-fluorophenyl)sulfonyloxy]phenyl, 3-[(4-fluorophenyl)sulfonyloxy]-4-nitrophenyl, 3-[(4-chlorophenyl)sulfonyloxy]-4-nitrophenyl,4-[(4-chlorophenyl)sulfonyloxy]phenyl, 4-[(4-bromophenyl)sulfonyloxy]phenyl, 4-(pyrid-4-ylcarbonyl)phenyl, 4-(4-carboxybenzoyl)phenyl, 4-(2-carboxybenzoyl)phenyl, 4-(2-bromobenzoyl)phenyl, 4-(3-bromobenzoyl)phenyl, 4-(3-methoxybenzoyl)phenyl, 4-(4-methoxybenzoyl)phenyl, 2-benzoylphenyl, 3-benzoylphenyl, 4-benzoylphenyl, 4-(4-chlorobenzoyl)phenyl, 4-(3-chlorobenzoyl)phenyl, 4-(4-cyanobenzoyl)phenyl, 4-(4-nitrobenzoyl)phenyl, 4-(4-methylbenzoyl)phenyl, 3-acetylphenyl, 4-acetylphenyl, 4-ethylcarbonylphenyl, 4-isobutylcarbonylphenyl, 4-cyclopropylmethylcarbonylphenyl, 3,4-diacetylphenyl, 3,5-diacetylphenyl, 5-acetyl-2-hydroxyphenyl, 3-(piperidin-1-ylcarbonyl)-phenyl, 4-(piperidin-1-yl-carbonyl)phenyl, 4-methoxycarbonylmethylphenyl, 4-(morpholin-4-ylmethyl)phenyl, 4-(4-methylpiperazin-1-ylmethyl)phenyl, 3-dimethylsulfamoyloxyphenyl, 4-dimethylsulfamoyloxyphenyl, 3chloro-4-dimethylsulfamoyloxyphenyl, 3-methylsulfonyloxy-4-nitrophenyl, 4-chloromethylphenyl, 3-chloromethylphenyl, 3-(phenylsulfonyl)phenyl, 4-(phenylsulfonyl)phenyl, 3-(4-methoxyphenoxy)phenyl, 3-(pyrid-4-yloxy)phenyl, 4-(pyrid-4-yloxy)phenyl, 3-pyrrolidinyl4-methoxyphenyl, 3-(pyrrolidin-2-on-1-yl)phenyl and 3-(pyrrolidin-2,5dion-1-yl)phenyl.

A further group of PDE4 inhibitors that may be employed in the present invention (hereinafter referred to as SELECTED PDE4 INHIBITORs—Embodiment D) includes compounds of Formula 3:

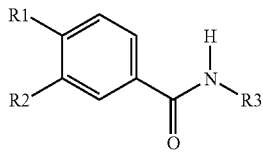

in which:
one of the substituents R1 and R2 is:
a 1-4C-alkoxy, a 3-5C-cycloalkoxy, a 3-5C-cycloalkylmethoxy, a benzyloxy or a 1-4C-alkoxy which is completely or partially substituted by fluorine, and
the other is 1-4C-alkoxy which is completely or partially substituted by fluorine; and
R3 is 2-bromophenyl; 2,6-dichloro-4-ethoxycarbonylphenyl; 2,6-dimethoxyphenyl; 4-cyano-2-fluorophenyl; 2,4,6-trifluorophenyl; 2-chloro-6-methylphenyl; 2,6- dimethylphenyl; 2,6-difluorophenyl; 2,6-dichlorophenyl; 3,5-dichloropyrid-4-yl; 3-methylpyrid-2-yl; 2-chloropyrid-3-yl; 3,5-dibromopyrid-2-yl; 2,3,5,6-tetrafluoropyrid-4-yl; 3-chloro-2,5,6-trifluoropyrid-4-yl; 3,5-dichloro-2,6-difluoropyrid-4-yl; or 2,6-dichloropyrid-3-yl;

and the salts of these compounds, and the N-oxides of the pyridines and their salts.

SELECTED PDE4 INHIBITORs—Embodiment D, which are to be emphasized include compounds of Formula 3, in which:
R1 is 1-4C-alkoxy which is completely or partially substituted by fluorine;
R2 is 3-5C-cycloalkylmethoxy or benzyloxy; and
R3 is 2-bromophenyl; 2,6-dichloro-4-ethoxycarbonylphenyl; 2,6-dimethoxyphenyl; 4-cyano-2-fluorophenyl; 2,4,6-trifluorophenyl; 2-chloro-6-methylphenyl; 2,6-dimethylphenyl; 2,6-difluorophenyl; 2,6-dichlorophenyl; 3,5-dichloropyrid-4-yl; 3-methylpyrid-2-yl; 2-chloropyrid-3-yl; 3,5-dibromopyrid-2-yl; 2,3,5,6-tetrafluoropyrid-4-yl; 3-chloro-2,5,6-trifluoropyrid-4-yl; 3,5-dichloro-2,6-difluoropyrid-4-yl; or 2,6-dichloropyrid-3-yl;

and the salts of these compounds, and the N-oxides of the pyridines and their salts.

Further SELECTED PDE4 INHIBITORs—Embodiment D, which are to be emphasized include compounds of Formula 3, in which:
R1 is difluoromethoxy;
R2 is methoxy, ethoxy, isopropoxy, isobutoxy, cyclopentyloxy, cyclopropylmethoxy, cyclobutylmethoxy, difluoromethoxy or 2,2,2-trifluoroethoxy; and
R3 is 2-bromophenyl; 2,6-dichloro-4-ethoxycarbonylphenyl; 2,6-dimethoxyphenyl; 4-cyano-2-fluorophenyl; 2,4,6-trifluorophenyl; 2-chloro-6-methylphenyl; 2,6-dimethylphenyl; 2,6-difluorophenyl; 2,6-dichlorophenyl; 3,5-dichloropyrid-4-yl; 3-methylpyrid-2-yl; 2-chloropyrid-3-yl; 3,5-dibromopyrid-2-yl; 2,3,5,6-tetrafluoropyrid-4-yl; 3-chloro-2,5,6-trifluoropyrid-4-yl; 3,5-dichloro-2,6-difluoropyrid-4-yl; or 2,6-dichloropyrid-3-yl;

and the salts of these compounds, and the N-oxides of the pyridines and their salts.

Specific SELECTED PDE4 INHIBITORs—Embodiment D, that may be employed in the present invention include the following compounds of Formula 3:

N-(3,5-Dichloropyrid-4-yl-4-difluoromethoxy-3-methoxybenzamide;

N-(3,5-Dichloropyrid-4-yl)-3,4-bis-difluoromethoxybenzamide;

N-(3,5-Dichloropyrid-4-yl)-3-cyclobutylmethoxy-4-difluoromethoxybenzamide;

N-(3,5-Dichloropyrid-4-yl)-3-cyclopentyloxy-4-difluoromethoxybenzamide;

N-(3,5-Dichloropyrid-4-yl)-3-cyclopropylmethoxy-4-difluoromethoxybenzamide;

N-(3,5-Dichloro-2,6-difluoropyrid-4-yl)-3-difluoromethoxy-4-methoxybenzamide;

N-(2,6-Dichlorophenyl)-3-difluoromethoxy-4-methoxybenzamide;

N-(2,6-Dimethylphenyl)-3-difluoromethoxy-4-methoxybenzamide;

N-(2-Chloropyrid-3-yl)-3-difluoromethoxy-4-methoxybenzamide;

N-(3,5-Dibromopyrid-2-yl)-3-difluoromethoxy-4-methoxybenzamide;

N-(3,5-Dichloropyrid-4-yl-3-difluoromethoxy-4-methoxybenzamide;

N-(3,5-Dichloropyrid-4-yl)-3-difluoromethoxy-4-propoxybenzamide;

N-(3,5-Dichloropyrid-4-yl)-3-ethoxy-4-difluoromethoxybenzamide;

N-(3,5-Dichloropyrid-4-yl-4-benzyloxy-3-difluoromethoxybenzamide;
N-(3,5-Dichloropyrid-4-yl)-4-butoxy-3-difluoromethoxybenzamide;
N-(3,5-Dichloropyrid-4-yl)-4-cyclopropylmethoxy-3-difluoromethoxybenzamide;
N-(3,5-Dichloropyrid-4-yl)-4-difluoromethoxy-3-(1-methylethoxy)benzamide;
N-(3,5-Dichloropyrid-4-yl-4-difluoromethoxy-3-(2,2,2-trifluoroethoxy)benzamide;
N-(3,5-Dichloropyrid-4-yl)-4-difluoromethoxy-3-(2-methylpropoxy)benzamide;
N-(2,3,5,6-Tetrafluoropyrid-4-yl)-4-difluoromethoxy-3-methoxybenzamide;
N-(2,4,6-Trifluorophenyl)-4-difluoromethoxy-3-methoxybenzamide;
N-(2,6-Dichloro-4-ethoxycarbonylphenyl)-4-difluoromethoxy-3-ethoxybenzamide;
N-(2,6-Dichlorophenyl)-4-difluoromethoxy-3-methoxybenzamide;
N-(2,6-Difluorophenyl)-4-difluoromethoxy-3-methoxybenzamide;
N-(2,6-Dimethylphenyl)-4-difluoromethoxy-3-methoxybenzamide;
N-(2-Bromophenyl)-4-difluoromethoxy-3-methoxybenzamide;
N-(2-Chloro-6-methylphenyl)-4-difluoromethoxy-3-methoxybenzamide;
N-(2-Chloropyrid-3-yl)-4-difluoromethoxy-3-methoxybenzamide;
N-(2-Methylphenyl)-4-difluoromethoxy-3-methoxybenzamide;
N-(3,5-Dibromopyrid-2-yl)-4-difluoromethoxy-3-methoxybenzamide;
N-(3,5-Dichloro-2,6-difluoropyrid-4-yl)-4-difluoromethoxy-3-methoxybenzamide;
N-(3-Chloro-2,5,6-trifluoropyrid-4-yl)-4-difluoromethoxy-3-methoxybenzamide; and
N-(3-Methylpyrid-2-yl)-4-difluoromethoxy-3-methoxybenzamide.

Salts encompassed within the term "pharmaceutically acceptable salts" refer to non-toxic salts of the compounds which are generally prepared by reacting a free base with a suitable organic or inorganic acid or by reacting the acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid, the acids being employed in salt preparation—depending on whether it is a mono- or polybasic acid and depending on which salt is desired—in an equimolar quantitative ratio or one differing therefrom. Preferred are in this connection the salts with hydrochloric acid.

As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

It is understood that the active compounds and their pharmaceutically acceptable salts mentioned can also be present, for example, in the form of their pharmaceutically acceptable solvates, in particular in the form of their hydrates.

The preparation of the SELECTED PDE4 INHIBITORs—EMBODIMENT A as well as their use as PDE4 inhibitors is described in WO00/42020. The preparation of the SELECTED PDE4 INHIBITORs—EMBODIMENT B as well as their use as phosphodiesterase (PDE) 4 inhibitors is described in WO02/064584 and WO2004/018450. The preparation of the SELECTED PDE4 INHIBITORs—EMBODIMENT C as well as their use as PDE4 inhibitors is described in WO97/28131, WO99/05111, WO00/42034 and WO02/06239.

It has now been found that the SELECTED PDE4 INHIBITORs mentioned above reduce the postprandial hyperglycemia and after prolonged treatment also the fasting hyperglycemia. This is an advantage to insulin secretagogues, biguanides and α-Glucosidase inhibitors which improve either fasting or postprandial hyperglycemia. In contrast to insulin and insulin secretagogues, the SELECTED PDE4 INHIBITORs do not induce hypoglycemia. Mice treated with the SELECTED PDE4 INHIBITORs mentioned above did not suffer highly increased lactate levels or keto acidosis, common adverse effects of biguanides. As well, anemia frequently accompanying rosiglitazone treatment were not observed.

Thus, a first aspect of the present invention is the use of a SELECTED PDE4 INHIBITOR in the production of a pharmaceutical composition for the treatment of diabetes mellitus.

A further aspect of the present invention is the use of a SELECTED PDE4 INHIBITOR in the production of a pharmaceutical composition for the treatment of diabetes mellitus and for the prevention of disorders which are related to diabetes mellitus.

A still further aspect of the present invention is the use of a SELECTED PDE4 INHIBITOR in the production of a pharmaceutical composition for the treatment of diabetes mellitus and for the prevention and/or treatment of disorders which are related to diabetes mellitus.

The invention further relates to a method for treating diabetes mellitus comprising administering to a patent in need thereof an effective amount of a SELECTED PDE4 INHIBITOR.

The invention additionally relates to a method for treating diabetes mellitus and for preventing disorders which are related to diabetes mellitus comprising administering to a patient in need thereof an effective amount of a SELECTED PDE4 INHIBITOR.

The invention as well relates to a method for treating diabetes mellitus and for preventing and/or treating disorders which are related to diabetes mellitus, comprising administering to a patient in need thereof an effective amount of a SELECTED PDE4 INHIBITOR.

Another aspect of the present invention is a method for reducing the postprandial hyperglycemia comprising administering to a patient in need thereof for a prolonged period of time an effective amount of a SELECTED PDE4 INHIBITOR.

Still another aspect of the present invention is a method for reducing the postprandial hyperglycemia comprising administering to a patient In need thereof for at least 5 days an effective amount of a SELECTED PDE4 INHIBITOR.

A further aspect of the present invention is a method for reducing fasting hyperglycemia, comprising administering to a patient in need thereof for a prolonged period of time an effective amount of a SELECTED PDE4 INHIBITOR.

Still a further aspect of the present invention is a method for reducing fasting hyperglycemia, comprising administering to a patient in need thereof for at least 5 days an effective amount of a SELECTED PDE4 INHIBITOR.

The invention also relates to a method for reducing the postprandial hyperglycemia and after prolonged treatment also the fasting hyperglycemia, comprising administering to a patient in need thereof an effective amount of a SELECTED PDE4 INHIBITOR.

The expressions "prolonged treatment" or "for a prolonged period of time" stand for a repeated administration of a SELECTED PDE4 INHIBITOR for at least 5 days.

The invention further relates to a ready to use pharmaceutical composition, comprising a SELECTED PDE4 INHIBITOR as active compound (=therapeutic agent), which contains a reference to the fact that this ready to use pharmaceutical composition can be employed in the treatment of diabetes mellitus and disorders which are related to diabetes mellitus.

The expressions "diabetes mellitus and accompanying disorders" or "diabetes mellitus and disorders which are related to diabetes mellitus" as used herein refers to type 1 diabetes (insulin-dependent diabetes mellitus, IDDM), type 2 diabetes (non-insulin-dependent diabetes mellitus, NIDDM), dyslipidemia, keto acidosis, the so called "metabolic syndrome", insulin resistance and obesitas. Subjects with diabetes manifest varying degrees of increased blood pressure, increased levels of cholesterol and/or triglycerides, increased levels of uric acid and increased levels of factors that promote coagulation. Therefore accompanying disorders of diabetes mellitus are hypertension, hyperlipidemia, hyperuricemia or gout and hypercoagulability, that means an abnormal, increased tendency to form clots inside blood vessels. These disorders are well-recognized risk factors for atherosclerotic macrovascular as well as microvascular diseases. Atherosclerotic macrovascular diseases include myocardial infarction, stroke and limb amputation. Microvascular complications involve blindness, renal diseases and debilitating neuropathies.

The SELECTED PDE4 INHIBITORs according to the invention may be administered in a variety of forms. These include, for example, liquid, semi-solid and solid dosage forms, such as liquid solutions (e.g., injectable and infusible solutions), dispersions or suspensions, tablets, pills, powders, liposomes or suppositories. The preferred form depends on the intended mode of administration and therapeutic application.

The most preferred mode of administration of a SELECTED PDE4 INHIBITOR is oral. In another preferred embodiment the SELECTED PDE4 INHIBITOR is administered by intravenous infusion or injection. In a further embodiment the SELECTED PDE4 INHIBITOR is administered by intramuscular or subcutaneous injection. Other routes of administration are also contemplated, including intranasal and transdermal routes, and by inhalation.

Typically, the SELECTED PDE4 INHIBITORs according to the invention will be administered in the form of a composition comprising the therapeutic agent in conjunction with pharmaceutically acceptable carriers. In this connection "pharmaceutically acceptable carrier" includes any and all solvents, dispersion media, coatings, antibacterial, and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life and the effectiveness of the therapeutic agent(s).

Therapeutic compositions typically must be sterile and stable under the condition of manufacture and storage. The composition can be formulated, for example, as a solution, microemulsion, dispersion, liposome, or other ordered structure suitable to high drug concentration.

Sterile injectable solutions can be prepared by incorporating the therapeutic agent(s) in the required amount in an appropriate solvent with one or a combination of ingredients enumerated above, as required, followed by filtered sterilization. Generally, dispersions are prepared by incorporating the therapeutic agent(s) into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the therapeutic agent(s) plus any additional desired ingredient from the previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent which delays absorption, for example, monostearate salts and gelatin.

In a preferred embodiment, the therapeutic agent(s) of the invention may be orally administered, for example, with an inert diluent or an assimilable edible carrier. The therapeutic agent(s) may also be enclosed in a hard or soft shell gelatine capsule or compressed into tablets. For oral therapeutic administration the therapeutic agent(s) may be incorporated with excipients and used in the form of ingestable tablets, buccal tablets, troches, capsules, elixirs, suspensions, syrups, wafers, and the like. To administer the therapeutic agent(s) according to the invention it may be necessary to coat the therapeutic agent(s) with, or co-administer with the therapeutic agent(s) with, a material to prevent its inactivation.

In certain embodiments, the therapeutic agent(s) may be prepared with a carrier that will protect the agent against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and poylactic acid. Many methods for the preparation of such formulations are generally known to those skilled in the art.

It is known to the person skilled in the art that the optimum dose of an active compound can vary as a function of the body weight, the age and the general condition of the patient, and his/her response behavior to the active compound.

The optimum dose necessary in each case and manner of administration of the active compound can easily be fixed by any person skilled in the art on the basis of his expert knowledge.

In case of oral or intravenous administration of a SELECTED PDE4 INHIBITOR, the daily dose will likely be in the range from 0.03 to 3 mg/kg body weight of the subject to be treated, preferably by once daily administration.

In one embodiment of the present invention the dosage for an adult patient for the SELECTED PDE4 INHIBITORs (−)-cis-8,9-Dimethoxy-6-(4-benzoylphenyl)-1,2,3,4,4a,10b-hexahydrophenanthridine, (−)-cis-8,9-Dimethoxy-6-[3,4-bis-(cyclopropylmethoxy)phenyl]-1,2,3,4,4a,10b-hexahydrophenanthridine, (+)-cis-8,9-Dimethoxy-6-(4-carboxyphenyl)-1,2,3,4,4a,10b-hexahydrophenanthridine and (−)-cis-6-[4-(2-Ethyl-2H-tetrazol-5-yl)-phenyl]-8,9-dimethoxy-1,2,3,4,4a,10b-hexahydrophenanthridine is in the range of 1 to 100 mg once daily, preferably in the range of 5 to 15 mg once daily.

In one embodiment of the present invention the dosage for an adult patient for the SELECTED PDE4 INHIBITORs (4aS,8aR)-4-(3,4-Dimethoxyphenyl)-2-(1-pyrimidin-2-yl-piperidin-4-yl)-4a,5,8,8a-tetrahydro-2H-phthalazin-1-one, (4aS,8aR)-4-(3,4-Dimethoxy-phenyl)-2-(1-pyridin-2-ylmethyl-piperidin-4-yl)-4a,5,8,8a-tetrahydro-2H-phthalazin-1-one or 2-{4-[(4aS, 8aR)-4-(3,4-Dimethoxyphenyl)-1-oxo-4a,5,8,8a-tetrahydro-1H-phthalazin-2-yl]-piperidin-1-yl}-acetamide is between 0.1 and 10 mg once daily, preferably between 0.5 and 2 mg once daily.

Pharmacology

Model

Female C57BLKS db/db mice obtained from M&B A/S (8680 Ry, Denmark) were used In the studies at 10 to 11 weeks of age. Mice were housed 10 per cage and allowed free access to water and chow (chow 3433, Provimi Kliba SA, 4303 Kaiseraugst, Switzerland).

Experimental Protocol

Mice were allowed to acclimate to the local animal facilities for 1 week and retro-orbital blood samples were obtained 3 to 7 days prior to the start of the study.

Mice were treated with vehicle or a selected PDE4 inhibitor compound once daily in the morning. The selective PDE4 inhibitor compounds to be tested were suspended in 4% methocel and applied via oral gavage using oral feeding & dosing needles (outer diameter: 1.5 mm, TSE GmbH, 61350 Bad Homburg, Germany). A volume of 10 ml/kg body weight was administered for each dose.

10 days studies: Mice were treated with vehicle or a selected PDE4 inhibitor compound once daily in the morning. On day 9, mice were fasted for 24 hours by removing chow 1 hour after drug application. On day 10, glucose tolerance was assessed by oral application of 1 g/kg/10 ml glucose. Blood was sampled 15 minutes after glucose application and levels of glucose (accu-chek, Roche Diagnostics GmbH, 68298 Mannheim, Germany) were measured.

56 days studies: Mice were treated with vehicle or a selected PDE4 inhibitor compound once daily in the morning. On day 55, mice were fasted for 24 hours by removing chow 1 hour after drug application. On day 56, fasting blood glucose levels were measured and glucose tolerance was assessed by oral application of 1 g/kg/10 ml glucose. Blood was sampled 15 minutes after glucose application and levels of glucose (accu-chek, Roche Diagnostics GmbH, 68298 Mannheim, Germany) and lactate (lactate reagent, Sigma-Aldrich GmbH, 82039 Deisenhofen, Germany) were measured.

Results

Table 1 illustrates blood glucose levels 15 minutes after glucose application. Mice were treated 10 days with (−)-cis-8,9-Dimethoxy-6-[3,4-bis-(cyclopropylmethoxy)phenyl]-1,2,3,4,4a,10b-hexahydrophenanthridine (COMPOUND A).

TABLE 1

|  | Blood glucose [mg/dl] |
| --- | --- |
| Vehicle (4% methocel) | 574 |
| COMPOUND A - 3 mg/kg | 507 |
| COMPOUND A - 30 mg/kg | 411.5 |

Table 2 illustrates blood glucose levels 15 minutes after glucose application. Mice were treated 10 days with (−)-cis-8,9-Dimethoxy-6-(4-benzoylphenyl)-1,2,3,4,4a,10b-hexahydrophenanthridine (COMPOUND B).

TABLE 2

|  | Blood glucose [mg/dl] |
| --- | --- |
| Vehicle (4% methocel) | 500 |
| COMPOUND B - 3 mg/kg | 362 |
| COMPOUND B - 30 mg/kg | 251 |

Table 3 illustrates blood glucose levels 15 minutes after glucose application. Mice were treated 10 days with (+)-cis-8,9-Dimethoxy-6-(4-carboxyphenyl)-1,2,3,4,4a,10b-hexahydrophenanthridine Hydrochloride (COMPOUND C).

TABLE 3

|  | Blood glucose [mg/dl] |
| --- | --- |
| Vehicle (4% methocel) | 584 |
| COMPOUND C - 3 mg/kg | 506 |
| COMPOUND C - 30 mg/kg | 449 |

Table 4 illustrates blood glucose levels 15 minutes after glucose application. Mice were treated 10 days with (−)-cis-6-[4-(2-Ethyl-2H-tetrazol-5-yl)-phenyl]-,8,9-dimethoxy-1,2,3,4,4a,10b-hexahydrophenanthridine (COMPOUND D).

TABLE 4

|  | Blood glucose [mg/dl] |
| --- | --- |
| Vehicle (4% methocel) | 490 |
| COMPOUND D - 3 mg/kg | 437 |
| COMPOUND D - 30 mg/kg | 285 |

Table 5 illustrates fasting blood glucose levels and blood glucose levels 15 minutes after glucose application. Mice were treated 56 days with COMPOUND A.

TABLE 5

|  | Blood glucose [mg/dl] | |
| --- | --- | --- |
|  | fasting | 15 min after glucose application |
| Vehicle (4% methocel) | 299 | 590 |
| COMPOUND A - 3 mg/kg | 279 | 580 |
| COMPOUND A - 30 mg/kg | 193 | 352 |

Table 6 illustrates fasting lactate levels in serum and lactate levels 15 minutes after glucose application. Mice were treated 56 days with COMPOUND A.

TABLE 6

| | Lactate [mg/dl] | |
|---|---|---|
| | fasting | 15 min after glucose application |
| Vehicle (4% methocel) | 51 | 49 |
| COMPOUND A - 3 mg/kg | 49 | 70 |
| COMPOUND A - 30 mg/kg | 43 | 61 |

SUMMARY

A 10 days treatment with SELECTED PDE4 INHIBITORs has been demonstrated to reduce postprandial blood glucose levels in db/db mice in accordance with the biochemical test methods detailed hereinbefore. A 56 days treatment with SELECTED PDE4 INHIBITORs resulted in reduced fasting and postprandial blood glucose levels with only moderate increases of postprandial lactate levels.

The invention claimed is:

1. A method for treating diabetes mellitus type 2 in a patient, comprising administering to a patient in need thereof an effective amount of N-(3,5-Dichloropyrid-4-yl)-3-cyclopropylmethoxy-4-difluoromethoxybenzamide.

2. The method of claim 1, wherein administering comprises administering the N-(3,5-Dichloropyrid-4-yl)-3-cyclopropylmethoxy-4-difluoromethoxybenzamide in a dosage form selected from the group consisting of an oral dosage form; an injectable dosage form; and an infusible dosage form.

3. The method of claim 2, wherein the dosage form comprises an oral dosage form.

4. The method of claim 2, wherein the dosage form comprises an injectable or an infusible dosage form.

5. A method for treating diabetes mellitus type 2 in a patient, comprising administering to a patient in need thereof an effective amount of a compound selected from the group consisting of N-(3,5-Dichloropyrid-4-yl)-3-cyclopropyl-methoxy-4-difluoromethoxybenzamide; a pharmaceutically acceptable salt thereof; an N-oxide thereof; and a pharmaceutically acceptable salt of an N-oxide thereof.

6. The method of claim 5, wherein said administering comprises administering the compound in a dosage form selected from the group consisting of an oral dosage form; an injectable dosage form; and an infusible dosage form.

7. The method of claim 6, wherein the dosage form comprises an oral dosage form.

8. The method of claim 6, wherein the dosage form comprises an injectable or an infusible dosage form.

* * * * *